(12) United States Patent
Dickinson

(10) Patent No.: US 6,378,362 B1
(45) Date of Patent: Apr. 30, 2002

(54) IN-SITU VADOSE ZONE REMOTE SENSOR

(76) Inventor: Larry Dickinson, 42125 S. Morton Rd., Kennewick, WA (US) 99337

( * ) Notice: Subject to any disclaimer, the term of this patent is extended or adjusted under 35 U.S.C. 154(b) by 0 days.

(21) Appl. No.: 09/694,732

(22) Filed: Oct. 23, 2000

(51) Int. Cl.⁷ .......................... E21B 49/00; G01N 1/16; G01N 33/24; C02F 3/00; C12Q 1/00

(52) U.S. Cl. ................ 73/152.28; 73/863.23; 436/32; 210/617; 205/777.5

(58) Field of Search ............... 73/152.28, 152.39, 73/864.74, 152.23, 863.23; 435/262; 436/32; 340/605; 175/20; 210/617; 702/23; 105/777.5

(56) References Cited

U.S. PATENT DOCUMENTS 5,085,499 A * 2/1992 Griffin et al. ............... 356/311
5,676,820 A * 10/1997 Wang et al. ............. 205/777.5
5,985,149 A * 11/1999 Raetz et al. ............... 210/617

* cited by examiner

Primary Examiner—Hezron Williams
Assistant Examiner—Jay L. Politzer
(74) Attorney, Agent, or Firm—Liebler, Ivey & Connor; Floyd E. Ivey

(57) ABSTRACT

This invention provides saturated and unsaturated Vadose zone remote sample acquisition and in-situ contaminant character identification. The invention is addressed to the management of the Vadose zone. Matters of interest to the agricultural community may include, in addition to other factors, the quantity of nutrients in the saturated zone and the existence of contaminants and the potential for loss of nutrients to the unsaturated zone. Matters of interest to facilities engaging in pollution, toxic or other contaminant detection will be the presence of such contaminants in both the saturated and unsaturated zones and additionally of the transit of contaminants into the unsaturated zone having potential of interaction with the water table. The unit acquires a sample of liquid transiting the vadose zone; sensors exposed to the liquid transmit data signals regarding the quantity and character is the liquid; liquid accumulated in a unit sump is periodically pumped to uncontaminated sample liquid storage for analysis and as a resource for replenishing the liquid proximal the sensors. All activities occurring within the unit are recorded or stored by storage or computer means; control means operates pumps.

6 Claims, 5 Drawing Sheets

IN-SITU VADOSE ZONE REMOTE SENSOR

FIELD OF THE INVENTION

This invention relates generally to an apparatus and method of remotely obtaining samples from and remotely detecting contaminants or constituents of soil in the vadose zone.

BACKGROUND OF THE INVENTION

The Vadose Zone is that region from the surface to the permanent water table. The portion generally viewed as the root zone is likely to contain moisture and may be titled the saturated zone. The character of the contents of the saturated zone is relatively easy to monitor by drilling permanent test wells and either pulling samples for analysis or installing sensors in the wells. The region below the root zone is unsaturated. Testing or characterizing the materials, perhaps contaminates or pollutants, from this portion of the vadose zone requires pulling 15 to 20 soil core samples in each area of interest, preparing the samples, e.g., by mixing the samples and sending the samples to a Lab for analysis. The sample acquisition in the unsaturated zone and analysis is time consuming and expensive. The unsaturated Vadose zone has always been the unknown area in the soil with those concerned often using their best estimate of the character or identification of and quantity of materials, i.e., contaminants, which were either situated to or were leaching through the soil toward the permanent water table.

The patents referred to herein are provided herewith in an Information Disclosure Statement in accordance with 37 CFR 1.97.

SUMMARY OF THE INVENTION

This invention provides saturated and unsaturated Vadose zone remote sample acquisition and in-situ contaminant character identification. The invention is addressed to the management of the Vadose zone. Matters of interest to the agricultural community may include, in addition to other factors, the quantity of nutrients in the saturated zone and the existence of contaminants and the potential for loss of nutrients to the unsaturated zone. Matters of interest to facilities engaging in pollution, toxic or other contaminant detection will be the presence of such contaminants in both the saturated and unsaturated zones and additionally of the transit of contaminants into the unsaturated zone having potential of interaction with the water table. The unit acquires a sample of liquid transiting the vadose zone; sensors exposed to the liquid transmit data signals regarding the quantity and character is the liquid; liquid accumulated in a unit sump is periodically pumped to uncontaminated sample liquid storage for analysis and as a resource for replenishing the liquid proximal the sensors. All activities occurring within the unit are recorded or stored by storage or computer means; control means operates pumps.

BRIEF DESCRIPTION OF THE DRAWINGS

The foregoing and other features and advantages of the present invention will become more readily appreciated as the same become better understood by reference to the following detailed description of the preferred embodiment of the invention when taken in conjunction with the accompanying drawings, wherein.

DETAILED DESCRIPTION

Figure 1:
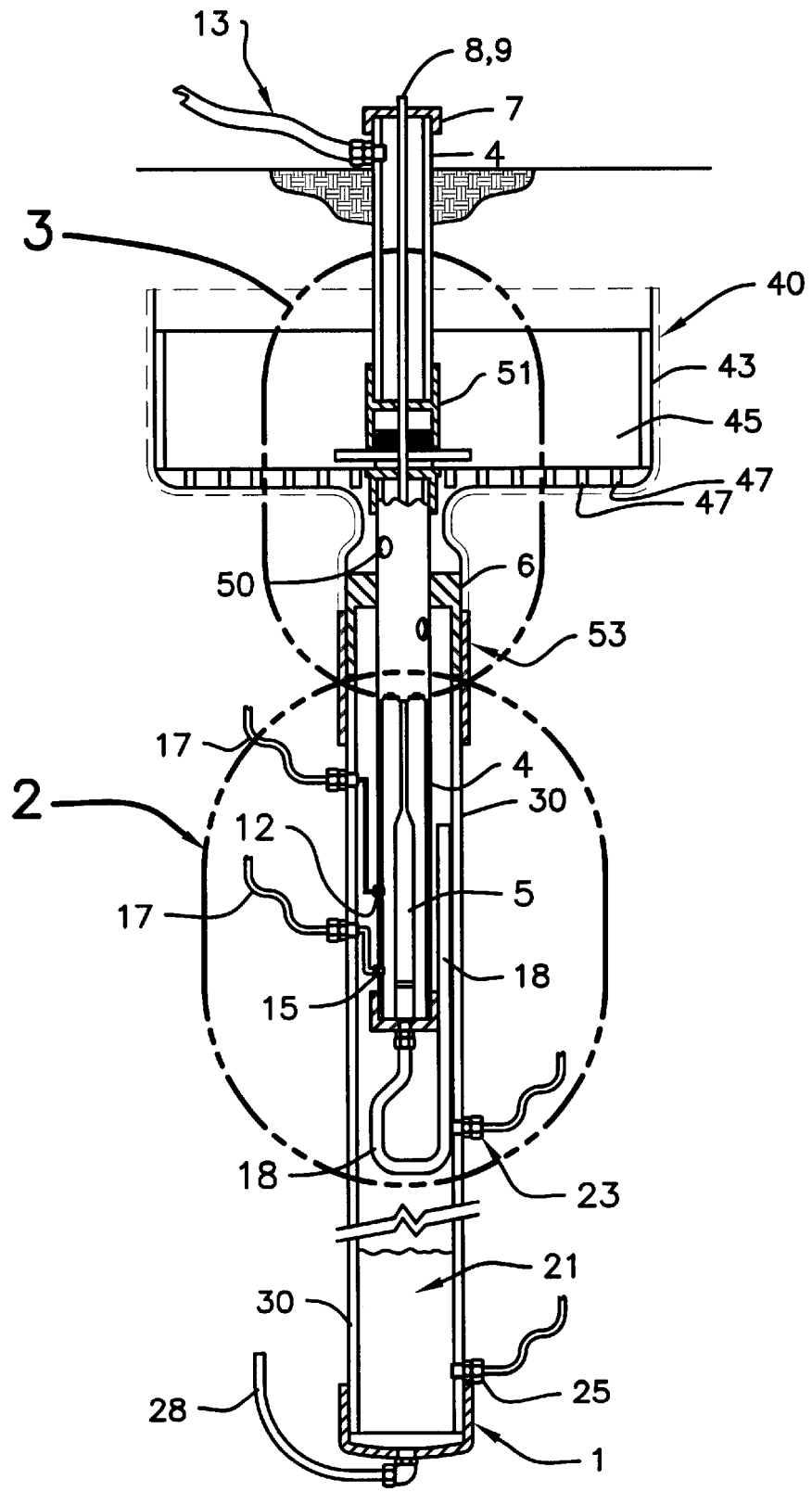
FIG. 1 is a front elevation of the In-Situ Vadose Zone Remote Sensor showing the sample collector assembly 40 with filter assembly 43, filter media 45 and filter support bars 47. Illustrated is the sensor receiver 2 with a cutaway presentation of the sensor receiver housing 4, at least one sensor 5, sensor receiver cap 7, sensor data lines 8 and sensor power 9. Seen is the remote sensor housing seal 6, top and lower conductivity switches 12, 15, conductivity switch connections 17, liquid injector line 13 and over flow tube 18. Also in within the sensor receiver housing 4 is seen a sensor receiver sample inlet 50, sensor receiver seal 51 and vacuum breaker 53. The remote sensor housing 30 is illustrated with sump 21, sump top and bottom conductivity snitches 23, 25.
Figure 2:
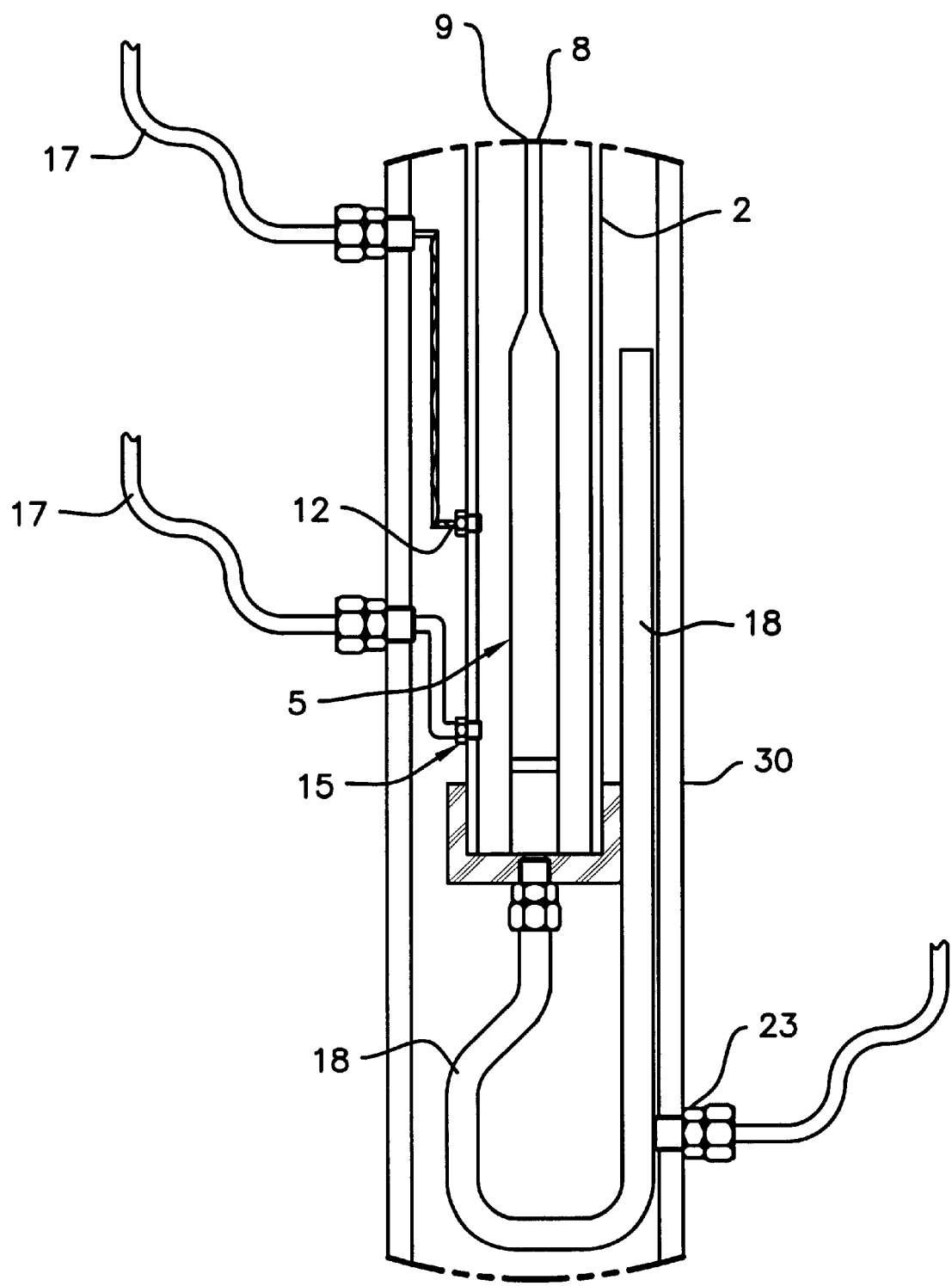
FIG. 2 is a cutaway detail from FIG. 1 showing the sensor receiver housing 4, at least one sensor 5, sensor receiver cap 7, sensor data lines 8 and sensor power 9. Seen is the remote sensor housing seal 6, top and lower conductivity switches 12, 15, conductivity switch connections 17, liquid injector line 13 and over flow tube 18. Also seen is remote sensor housing 30 and sump top conductivity switch 23.
Figure 3:
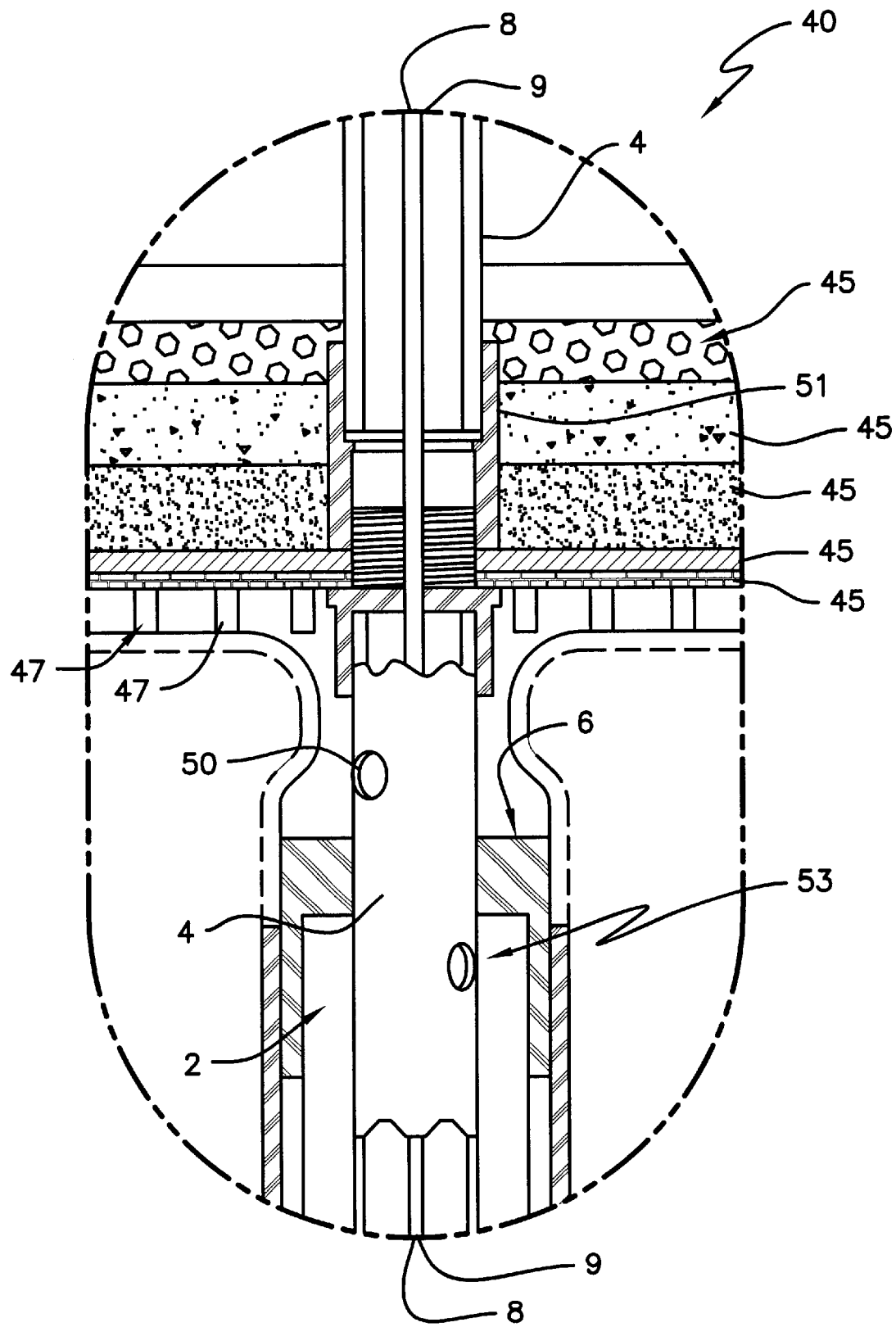
FIG. 3 is a detail cross-section from FIG. 1 showing the sample collector assembly 40 with filter assembly 43, filter media 45 and filter support bars 47. Illustrated is the sensor receiver 2 with a cutaway presentation of the sensor receiver housing 4, sensor data lines 8 and sensor power 9, sensor receiver sample inlet, sensor receiver seal 51 and vacuum breaker 53. Seen is the remote sensor housing seal 6.
Figure 4:
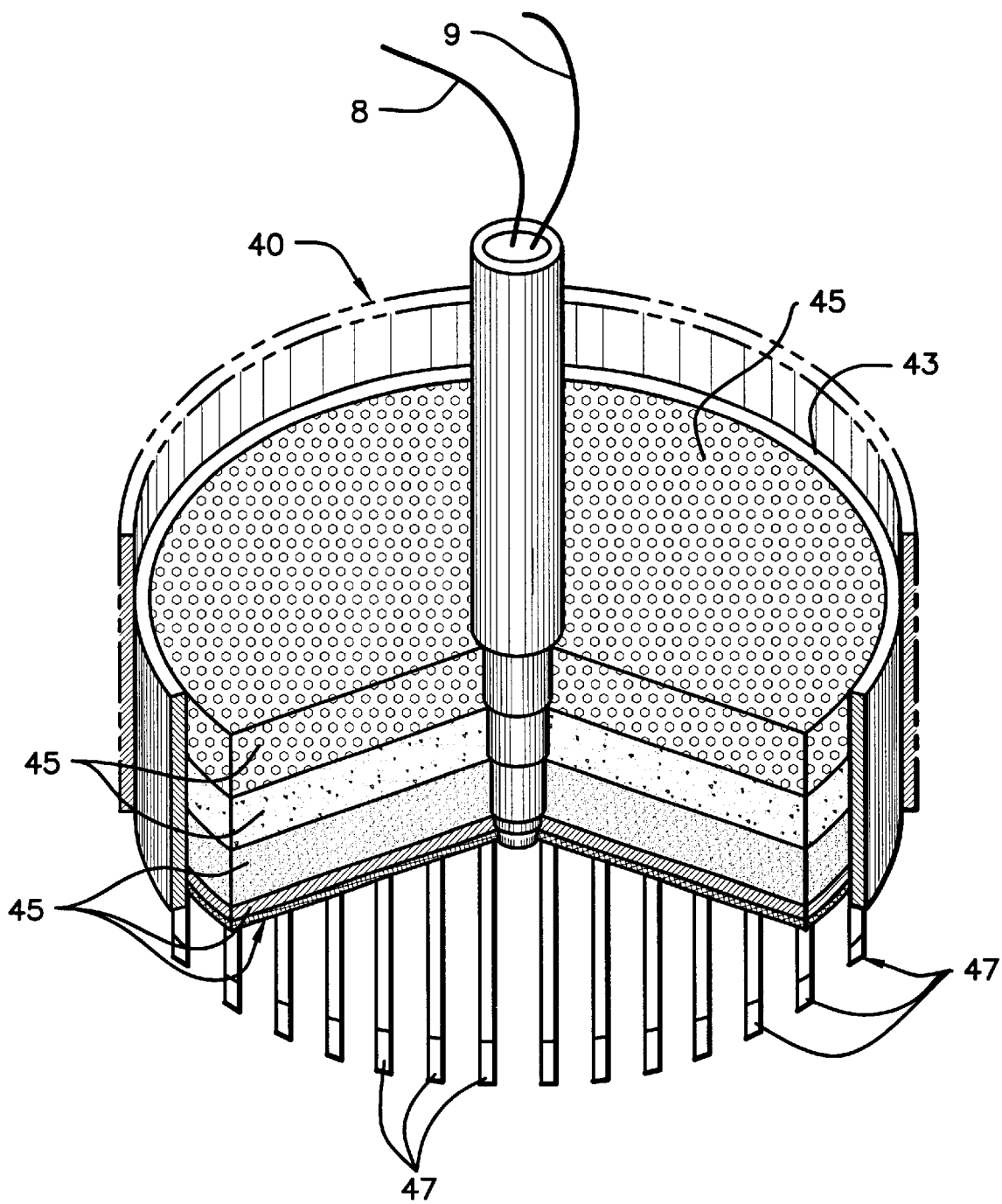
FIG. 4 is cut away depiction of the filter assembly 43, filter media 45 and filter support bars 47.

The In-Situ Vadose Zone Remote Sensor 1 of this invention is illustrated in FIGS. 1 through 5. The In-Situ Vadose Zone Remote Sensor 1 contains sensors 5 capable of detecting and of delivering a signal indicating the presence and quantity of a material or materials present which are of interest to the operator. A sample collector assembly 40 intercepts, collects and filters liquids transiting through the soil. The filtered sample liquid enters the a sensor receiver housing 4; the filtered sample liquid contacts sensors 5 within the sensor receiver 2 and sensor receiver housing 4. The one or a plurality of sensors 5 deliver a data signal to a data storage means and or a controller means 70. Detector or switch means insure proper operational levels of liquids within a sensor receiver housing 4 and separately within a remote sensor housing 30. The one or a plurality of sensors 5 may be subject to damage if the liquid level drops causing overheating of the sensors 5; at least one detector or switch means within the sensor receiver housing 4, provided for example by conductivity switches, float controlled switches or other switching means recognized by those of ordinary skill in switching arts, will detect an unacceptable liquid level in relation to the one or a plurality of sensors 5 and will, upon activation, such as opening, closing or detecting conductivity, provide an output to a data storage means and or a controller means 70; such level detection within the sensor receiver housing 4 may be comprised of a top conductivity switch and a lower conductivity switch 12, 15. The top conductivity switch 12 fulfilling the purpose of detecting a liquid level dropping below the desired operating level for the one or a plurality of sensors 5; an output from the top conductivity switch 12 will cause a pumping of liquid to the sensor receiver housing 4 via a liquid line injector 13, delivered, in the preferred embodiment, in 5 ml increments and delivered in a time delay sequence until such time as the top conductivity switch 12 again detects liquid. The lower conductivity switch 15, positioned at a lower level, indicates a failure; an output from the lower conductivity switch 15 to data storage means and or controller means 70 will cause an output from the data storage means and or controller means 70 to turn power off to the one or a plurality of sensors 5 and will create a command to alarm 80 the system operator. The liquid level of liquids received into the sensor receiver housing 4 is fixed by an overflow tube 18 which exits the sensor receiver housing 4 at a point below the operating level desired for liquids within the sensor receiver housing 4 with the overflow tube 18 exit placed within the remote sensor housing 30. The liquid exiting the sensor receiver housing 4 via the overflow tube 18 is deposited into the remote sensor housing sump 21.

The level of liquid received into the sump 21 is controlled by switch means provided for example by one or more conductivity switches, float controlled switches or other switching means recognized by those of ordinary skill in switching arts; such one or more switch means will detect an upper liquid level in relation to the sump and will, upon activation, such as opening, closing or detecting conductivity, provide an output to a data storage means and or a controller means; such level detection within the remote sensor housing 30 at the sump 21 may be comprised of a sump top and bottom conductivity switch 23, 25. The sump top conductivity switch 23 fulfilling the purpose of detecting a liquid level rising to the desired operating level for pumping the sump 21 to uncontaminated sample liquid storage 60; the sump top conductivity switch 23 providing an output to data storage means and or controller means 70; a sump bottom conductivity switch 25 fulfilling the purpose of detecting a liquid level indicating uncontaminated sample liquid available for pumping to the uncontaminated sample liquid storage 60; the sump bottom conductivity switch 25 providing an output to control and data storage means 70.

A micro-controller/microprocessor such as an Intel 8051 or other microprocessors and other devices and circuits recognized by those of ordinary skill in the data acquisition and control arts will provide data storage means and or controller means 70; such microprocessor function will apply in each instance for this invention where reference is found to data storage and or controller functions; control means will principally provide on or off input to a control system provided, for example by a Programmable Logic Controller(PLC) which will provide control signals to operate pumps, provide power and perform other tasks recognized by those of ordinary skill in control arts.

Sealing means prevents unwanted materials from entering the sensor receiver 2 intermediate the soil surface and the filter support bars 47. Sealing means, seen in FIG. 1 is sensor receiver seal 51 composed, for example of threaded couplers, including PVC couplers, and washers. A separate sealing means prevents unwanted entry of sample into the sensor receiving housing 4 and is shown in FIG. 1 as remote sensor housing seal 6 which functions additionally as a reducer or support structure between the sensor receiver housing 4 and the remote sensor housing 30. Filter support bars 7 may be composed of metal or plastic structures which will allow the filer media 45 to be supported. Intermediate the filter support bars 7 and remote sensor housing seal 6 is an aperture in the sensor receiver housing 4, denominated sensor receiver sample inlet 50, for the purpose of allowing the collected sample to pass into the sensor receiver sample housing 4. Another aperture within the sensor receiver housing 4, identified as the vacuum breaker 53, is proximal the remote sensor housing seal 6 and intermediate the remote sensor housing seal 6 and the one or a plurality of sensors 5. The vacuum breaker 53 functions to prevent the withdrawal of liquid within the sensor receiver housing 4 when vacuum pumping occurs via the sump pump out line 28 of the sump 21.

Figure 5:
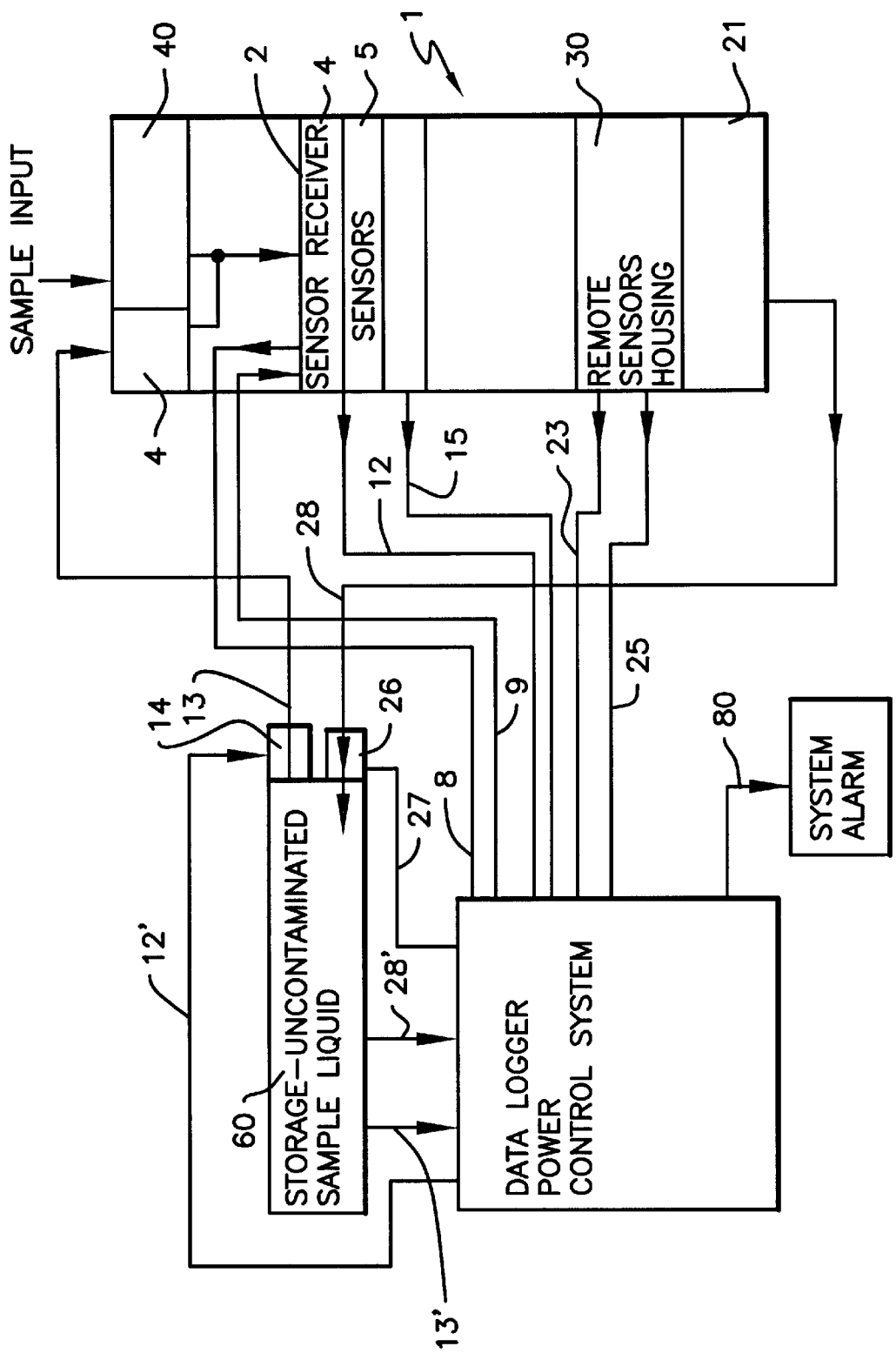
FIG. 5 is a flow chart showing the data and control interconnections of the In-Situ Vadose Zone Remote Sensor. Illustrated are the sample collector assembly 40 receiving a sample input, sensor receiver 2 and sensor receiver housing 4 with sensors 5; shown is the remote sensor housing 30 and sump 21. Outputs from at least one sensor 5 is illustrated to be received to a data storage means and or a controller means 70. Level detection means within the sensor receiver housing 4 and within the remote sensor housing 30 are depicted as providing outputs to a data storage means and or a controller means 70; additionally seen are level detection means for a remote sensor housing 30 which provide output for the purpose of control of the sample liquid collected in the sump with this level detection, as output to the data storage means and or a controller means 70 operating a sump vacuum pump to pump acquired sample liquid to uncontaminated sample storage and provide data.

The sample acquisition and system action and reactions include the following: the liquid passes through the preselected filter media 45 where any sensor fouling particles are filtered. Filter media 45 is determined by analysis of soil samples from the vadose zone of interest. Soil samples are taken, subjected to a flow through container with appropriate liquid flushed through and collected for analysis. The results of this analysis are used to determine the filter media 45. From the filter assembly 43, the sample liquid enters the sample collector assembly 40 and then flows into the sensor receiver 2 and sensor receiver housing 4, as shown in FIGS. 1 and 5. The sensor receiver 2 contains one or a plurality of sensors 5; in one embodiment from 1 to 9 real time sensors 5 are positioned which transmit data or information via cable data sensor lines 8 to data storage means and or controller means 70. Data storage of the generally mv output from the one or a plurality of sensors 5 are stored in said Data storage means and or controller means 70 for data analysis availability and for auditing purposes which may be required in meeting certain regulatory requirements related in particular to site monitoring in relation to clean up requirements of EPA or other political agencies. From the data storage means and or controller means 70 data is expected to be transmitted to a computer for storage and analysis with transmission by transmission means including but not limited to telephone lines, direct cable, or radio telemetry for data analyzing and storage. The sensors 5 cannot be allowed to run dry without damage and hence are subject to protection by at least one detection or switch means provided, for example by a top conductivity switch 12. When the liquid lowers to the level of the top conductivity switch 12, within the sensor receiver housing 4, the top conductivity switch 12 will loose contact with this detected by the data storage means and or controller means 70 with this signal stored and additionally with the data storage means and or controller means 70 which operates a liquid injector pump 14 via a liquid injector pump command 12'; this introduces, at the liquid injector line 13 input into the sensor receiver housing 4, liquid from the uncontaminated sample liquid storage 60; in the preferred embodiment a time relay will repeatedly cause addition of liquid in 5 ml increments into the sensor receiver housing 5, through the sensor receiver housing 5 above the sample collector assembly 40, until the top conductivity switch 12 is again in contact with liquid. If for some reason liquid is not being received into the sensor receiver housing 4 and the liquid level reaches the lower conductivity switch 15, this switch will provide an output to the data storage means and or controller means 70 which is recorded and which in turn cuts off power to the sensor power 9 and sends an alarm 80 message for service. The liquid exits the sensor receiver housing 4 via the an overflow tube 18 where the overflow tube 18 exits the sensor receiver housing 4 at a level below the level of liquid desired within the sensor receiver housing 4 for operational needs. The overflow tube 18, in the preferred embodiment is comprised of Stainless Steel. However other embodiments may have the over flow tube 18 and other components of the In-Situ Vadose Zone Remote Sensor composed of other materials including, for example plastics, metals, PVC and as well, Stainless Steel. The liquid exiting the overflow tube 18 enters the remote sensor housing sump 21. The sump has at least one level control switch means and in the preferred embodiment has two conductivity switches in the form of sump top and bottom conductivity switches 23, 25. The sump bottom conductivity switch 23 output is data for the data storage means and or controller means 70 that liquid is available for quality analysis and volume metric measurements of the event that created the flow of sample liquid into the sample collector assembly 40. This liquid is also desired for analytical proofing or calibrating of the sensors 5. The sump top conductivity switch 23 output to the data storage means and or controller means 70 results in a sump vacuum pump command 27 causing a sump vacuum pump 26 to operate to pump the liquid in the sump to a uncontaminated sample liquid storage 60 for subsequent storage and volumetric measurements and other analysis.

Sensors may include sensor means including but not limited to devices which detect and provide electrical responses in the presence of materials within the sample liquid including but not limited to nitrates, potassium mercury, heavy metals and other materials of agricultural and pollution interests.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. An In-Situ Vadose Zone Remote Sensor comprised of:
   A. a sample collector assembly 40 which intercepts, collects and filters liquids transiting through the soil; the filtered sample liquid enters a sensor receiver housing 4 connected to the sample collector assembly 40; the sensor receiver housing 4 containing one or a plurality of sensors 5; the one or a plurality of sensors 5 deliver a data signal via sensor data lined 8 to a microprocessor; detector or switch means insure proper operational levels of liquids within a sensor receiver housing 4 and separately within a remote sensor housing 30;
   B. at least one detector or switch means within the sensor receiver housing 4 to detect an unacceptable liquid level in relation to the one or a plurality of sensors 5 and will, upon activation, of opening, closing or detecting conductivity, provide an output to a microprocessor; said level detection within the sensor receiver housing 4 comprised of a top conductivity switch and a lower conductivity switch (12), (15); the top conductivity switch 12 fulfilling the purpose of detecting a liquid level dropping below the desired operating level for the one or a plurality of sensors 5; an output from the top conductivity switch 12 will cause a pumping of liquid to the sensor receiver housing 4 via a liquid line injector 13, delivered in 5 ml increments and delivered in a time delay sequence until such time as the top conductivity switch 12 again detects liquid; the lower conductivity switch 15, positioned at a lower level, indicates a failure; an output from the lower conductivity switch 15 to a microprocessor will cause an output from the microprocessor to turn power off to the one or a plurality of sensors 5 and will create a command to alarm 80 the system operator;
   C. the liquid level of liquids received into the sensor receiver housing 4 is fixed by an overflow tube 18 which exits the sensor receiver housing 4 at a point below the operating level desired for liquids within the sensor receiver housing 4 with the overflow tube 18 exit placed within the remote sensor housing 30; the liquid exiting the sensor receiver housing 4 via the overflow tube 18 is deposited into a remote sensor housing sump 21; the level of liquid received into the sump 21 is controlled by switch means by one or more conductivity switches, float controlled switches or other switching means; such one or more switch means will detect an upper liquid level in relation to the sump and will, upon activation, of opening, closing or detecting conductivity, provide an output to a microprocessor; such level detection within the remote sensor housing 30 at the sump 21 is comprised of a sump top and bottom conductivity switch 23, 25; the sump top conductivity switch 23 fulfilling the purpose of detecting a liquid level rising to the desired operating level for pumping the sump 21 to uncontaminated sample liquid storage 60; the sump top conductivity switch 23 providing an output to a microprocessor; a sump bottom conductivity switch 25 fulfilling the purpose of detecting a liquid level indicating uncontaminated sample liquid available for pumping to the uncontaminated sample liquid storage 60; the sump bottom conductivity switch 25 providing an output to control and data storage means 70;
   D. control means will principally provide on or off input to a control system provided, by a Programmable Logic Controller(PLC) or microprocessor which will provide control signals to operate pumps, provide power and perform other tasks recognized by those of ordinary skill in control arts.

2. An In-Situ Vadose Zone Remote Sensor comprised of:
   A. a sample collector assembly (40) which intercepts, collects and filters liquids transiting through the soil; the filtered sample liquid enters a sensor receiver housing (4) connected to the sample collector assembly (40); a sensor receiver (2) within the sensor receiver housing (4) containing one or a plurality of sensors (5); the one or a plurality of sensors (5) deliver a data signal via sensor data lines (8) to a microprocessor; detector or switch means insure proper operational levels of liquids within the sensor receiver housing (4) and separately within a remote sensor housing (30).

3. An In-Situ Vadose Zone Remote Sensor of claim 2 further comprised of:
   A. at least one level detector or switch means within the sensor receiver housing (4) to detect an unacceptable liquid level in relation to the one or a plurality of sensors (5) which provide an output to a microprocessor; the sensor receiver housing (4) received into and contained by the remote sensor housing (30);
   B. the liquid level of liquids received into the sensor receiver housing (4) is fixed by an overflow tube (18); the liquid exiting the sensor receiver housing (4) via the overflow tube (18) is deposited into a remote sensor housing sump (21) within the remote sensor housing (30);

C. control means will principally provide on or off input to a control system 18 provided by a Programmable Logic Controller(PLC) or a microprocessor which will provide control signals to operate pumps, provide power and perform other tasks.

4. An In-Situ Vadose Zone Remote Sensor of claim 3 further comprised of:

A. the at least one level detector or switch means within the sensor receiver housing (4) provided by conductivity switches, float controlled switches or other switching means which will, upon activation, of opening, closing or detecting conductivity provide an output to a microprocessor;

B. said overflow tube (18) exits the sensor receiver housing (4) at a point below the operating level desired for liquids within the sensor receiver housing (4) with the overflow tube (18) exit placed within the remote sensor housing (30); the level of liquid received into the sump (21) is controlled by switch means; such one or more switch means will detect an upper liquid level in relation to the sump and will, upon activation, of opening, closing or detecting conductivity, provide an output to a microprocessor means causing a pumping of liquid from the sump (21) via a sump pump out line (28).

5. An In-Situ Vadose Zone Remote Sensor of claim 4 further comprised of:

A. said level detection within the sensor receiver housing (4) comprised of a top conductivity switch and a lower conductivity switch (12), (15); the top conductivity switch (12) fulfilling the purpose of detecting a liquid level dropping below the desired operating level for the one or a plurality of sensors (5); an output from the top conductivity switch (12) will cause a pumping of liquid to the sensor receiver housing (4) via a liquid line injector (13) until such time as the top conductivity switch (12) again detects liquid; the lower conductivity switch (15), positioned at a lower level, indicates a failure; an output from the lower conductivity switch (15) to a microprocessor will cause an output from the microprocessor to turn power off to the one or a plurality of sensors (5) and will create a command to alarm (80) the system operator;

B. switch means controlling the sump (21) is by one or more conductivity switches, float controlled switches or other switching means.

6. An In-Situ Vadose Zone Remote Sensor of claim 5 further comprised of:

A. the pumping of liquid to the sensor receiver housing (4) via a liquid line injector (13), delivered in 5 ml increments and delivered in a time delay sequence until such time as the top conductivity switch (12) again detects liquid;

B. switch means controlling the sump (21) of one or more conductivity switches, float controlled switches or other switching means comprises level detection within the remote sensor housing (30) at the sump (21) and is comprised of a sump top and bottom conductivity switch (23), (25); the sump top conductivity switch (23) fulfilling the purpose of detecting a liquid level rising to the desired operating level for pumping the sump (21) to uncontaminated sample liquid storage (60); the sump top conductivity switch (23) providing an output to a microprocessor; the sump bottom conductivity switch (25) fulfilling the purpose of detecting a liquid level indicating uncontaminated sample liquid available for pumping to the uncontaminated sample liquid storage (60); the sump bottom conductivity switch (25) providing an output to control and data storage means (70);

C. a filter assembly (43) having filter media (45) and filter support bars (47) at the sample collector assembly (40) which intercepts, collects and filters liquids; sealing means prevents unwanted materials from entering the sensor receiver (2) intermediate the soil surface and the filter support bars (47); a separate sealing means prevents unwanted entry of sample into the sensor receiving housing (4) comprised of a remote sensor housing seal (6) which functions additionally as a reducer or support structure between the sensor receiver housing (4) and the remote sensor housing (30); intermediate the filter support bars (47) and remote sensor housing seal (6) is an aperture in the sensor receiver housing (4), denominated sensor receiver sample inlet 50, for the purpose of allowing the collected sample to pass into the sensor receiver sample housing (4); an aperture within the sensor receiver housing (4) comprising a vacuum breaker 53, is proximal the remote sensor housing seal (6) and intermediate the remote sensor housing seal (6) and the one or a plurality of sensors (5); the vacuum breaker 53 functioning to prevent the withdrawal of liquid within the sensor receiver housing (4) when vacuum pumping occurs via the sump pump out line (28) of the sump (21).

* * * * *